(12) United States Patent
Al-Lamee et al.

(10) Patent No.: US 6,369,168 B1
(45) Date of Patent: Apr. 9, 2002

(54) INTRODUCING FUNCTIONAL GROUPS TO A POLYMER

(75) Inventors: Kadem Gayad Al-Lamee, Leeds; Yousef Samih Taktak, Matlock, both of (GB)

(73) Assignee: Polybiomed Limited, Sheffield (GB)

( * ) Notice: Subject to any disclaimer, the term of this patent is extended or adjusted under 35 U.S.C. 154(b) by 0 days.

(21) Appl. No.: 09/425,823

(22) Filed: Oct. 22, 1999

Related U.S. Application Data

(63) Continuation of application No. PCT/GB98/01213, filed on Apr. 24, 1998.

(30) Foreign Application Priority Data

Apr. 25, 1997 (GB) .............................................. 9708325

(51) Int. Cl.⁷ .................................................. C08F 8/06
(52) U.S. Cl. ................. 525/376; 525/331.5; 525/333.6; 525/393.7; 525/333.8; 525/420; 525/453; 525/467
(58) Field of Search ............................... 525/376, 420, 525/453, 467

(56) References Cited

U.S. PATENT DOCUMENTS

| | | |
|---|---|---|
| 3,458,597 A | 7/1969 | Jabloner |
| 3,870,692 A | 3/1975 | Patton |
| 4,042,644 A | 8/1977 | Hrabak et al. |
| 4,923,931 A | 5/1990 | Pennington et al. |
| 5,064,908 A | 11/1991 | Schuster et al. |
| 5,344,455 A | 9/1994 | Keogh et al. |
| 5,356,433 A | 10/1994 | Rowland et al. |

FOREIGN PATENT DOCUMENTS

| | | |
|---|---|---|
| DE | 3436876 | 10/1984 |
| EP | 0065366 | 4/1982 |
| EP | 0572028 | 5/1993 |
| EP | 0661309 | 7/1995 |
| GB | 1184821 | 2/1967 |
| GB | 2113692 | 8/1983 |
| WO | 9117046 | 11/1991 |
| WO | 9325587 | 12/1993 |

*Primary Examiner*—Bernard Lipman
(74) *Attorney, Agent, or Firm*—Baker Botts L.L.P.

(57) ABSTRACT

A polymer, possibly fabricated as part of a medical device or as part of a medical prostheses (such as a contact lens) is functionalized to facilitate the introduction of functional groups, such as biomedical species including heparin. The polymer is reacted in an aqueous medium with a water soluble azo compound (such as cyanovaleric acid or 2-methylpropionamidine) to produce oxygen centered radicals responsible for introducing functional groups into the polymer.

10 Claims, 16 Drawing Sheets

INTRODUCING FUNCTIONAL GROUPS TO A POLYMER

This is a continuation of copending application Ser. No. PCT/GB98/01213 filed Apr. 24, 1998 which is incorporated by reference herein.

FIELD OF THE INVENTION

The present invention relates to a method and apparatus for substitution of functional groups on polymers, which may be suitable for functionalisation of medical devices. More particularly it relates to treatment of polymers which do not contain functional groups normally considered to be readily reactive. The invention also relates to further treatment of substituted polymers wherein, for example, monomers, polymers, biomolecular species and dyes may be grafted onto the substituted polymer.

INTRODUCTION TO THE INVENTION

Mechanical properties of synthetic polymers are such that they can be tailored for use in a wide range of applications in the field of biomaterials. However biocompatibility is often a problem Thus for example such materials frequently exhibit poor haemocompatiblity, excessive complement activation, sensitivity to bacterial attack, and poor tissue compatibility and so on. Such surface properties can be modified by functionalisation of the polymer surfaces. Processes for functionalisation of polymer surfaces are known, as for example described in European patent publication No EP 0643730. The method described consists of functionalisating of a polymer wherein the polymer is reacted in an aqueous medium with an oxidising agent to produce oxygen centred radicals which are responsible for introducing hydroxyl groups into the polymer. The reaction is carried out in the absence of (a) added oxygen, (b) a cationic surfactant and (c) any additive which is preferentially oxidised or is reactive toward the radical as produced by the oxidising agent. The oxidising agent used is a peroxy salt of a metal, preferably a peroxy-disulphate or monosulphate. This method produces hydroxyl radicals from decomposition of the peroxy oxidising agent The method overcomes certain disadvantages of pre-existing methods (for example action of high energy radiation, photo initiation, surface flaming etc) such as for example reducing the severity of degradation of the polymer and allowing processing to be undertaken in aqueous media. However, a problem with existing methods for functionalisation of a polymer, is that the amount of degradation is more than ideal. Furthermore, processing time tends to be long and the amount of oxidising agent required is generally considerable. Additionally known systems tend to involve many side reactions delaying formation of required functional groups and side products tend to interfere with the polymeric material, thus enhancing degradation.

From the above it is clear that there is a requirement for a method and apparatus for substitution of functional groups on a polymer, wherein polymeric degradation is reduced and reaction times are speeded up.

SUMMARY OF THE INVENTION

According to a first aspect of the present invention, there is provided a method of producing a functionalised polymer, comprising steps of reacting a polymer in aqueous medium with a water soluble azo compound to produce oxygen-centred radicals, wherein said radicals are responsible for introducing functional groups into the polymer.

In a preferred embodiment, the polymer is selected from the group consisting olefin, aliphatic polymers, polymers that contain an aromatic ring, carbonate polymers, vinyl polymers, polyurethanes, nylons, polyglycols or polyaldehydes.

Preferably, the method is carried out in the absence of any additive which is preferentially oxidised or is reactive towards the radicals produced by the azo compounds. Preferably, no cationic surfactants are added but an additional oxidising agent may be added, possibly in the form of oxygen gas.

According to a second aspect of the present invention, there is provided apparatus for producing a functionalised polymer, configured to react a polymer in aqueous medium with a water soluble azo compound to produce oxygen-centred radicals, wherein said radicals are responsible for introducing functional groups into the polymer.

Preferably, the apparatus is configured to produce a functionalised polymer in which said azo compound is 4,4'-azobis (cyanovaleric acid) or 2,2'-azobis (2-methylpropionamidine) dihydrochloride.

Preferably, the apparatus is configured to attach a biomolecular species (such as heparin) to the functionalised polymer. The functionalised polymer may be fabricated as a medical device, such as a blood pump etc or as a prosthetic device such as a contact lens.

DETAILED DESCRIPTION OF THE PREFERRED EMBODIMENTS

The invention will now be described by way of example only with reference to the previously identified drawings.

Figure 1:
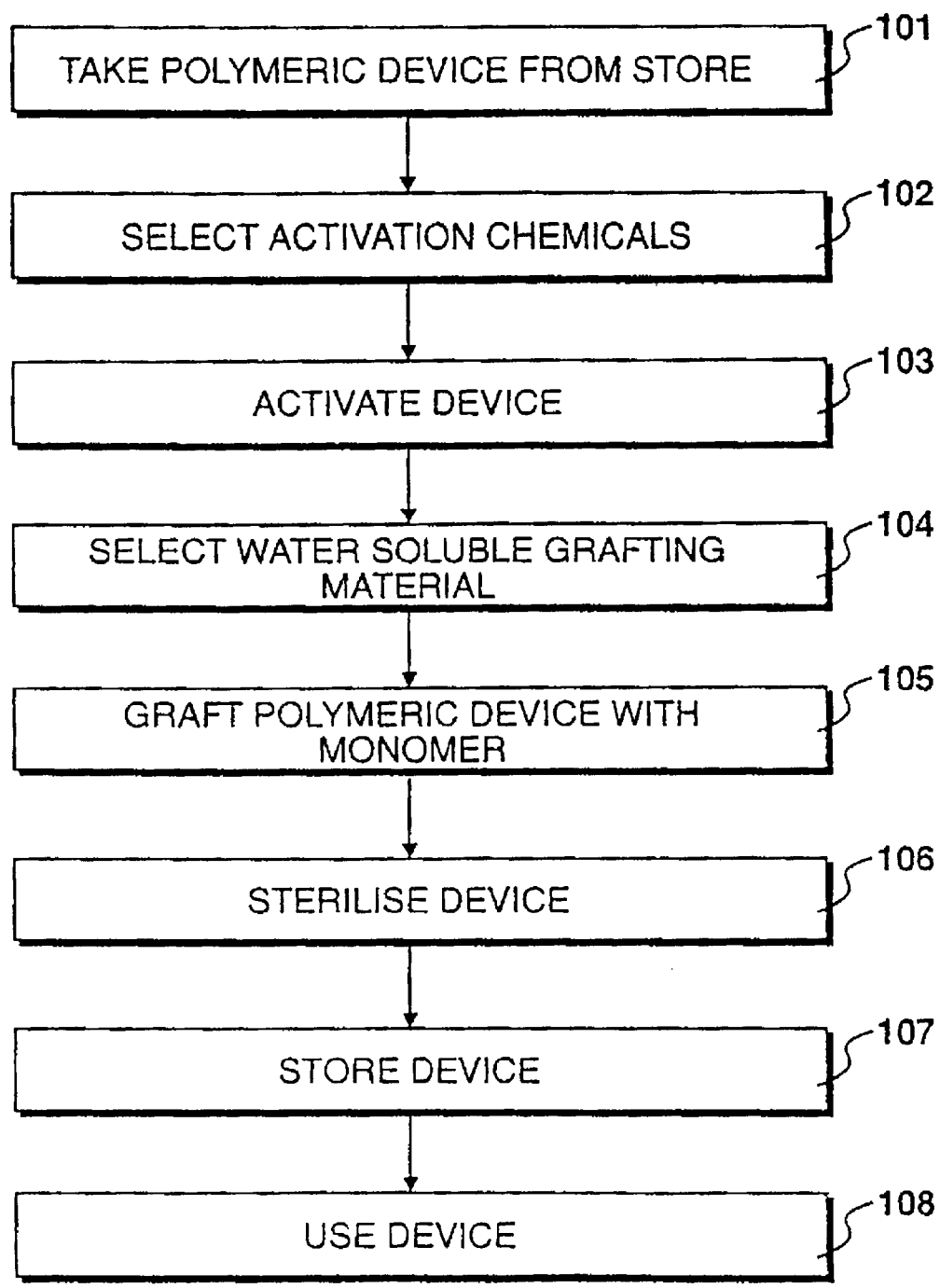
FIG. 1 shows an overview for the activation of a polymeric device including an activation step and a grafting step.

An overview of the method of substituting, in an aqueous medium, functional groups on a polymer with required functional groups is shown in FIG. 1. Initially polymeric material, possibly in the form of a device, is taken from store at step 101, whereafter at step 102 activation chemicals to facilitate a said substitution are selected. At step 103 the selected polymeric device is activated via treatment with the selected activation chemicals selected in step 102. Following activation at step 103, the polymeric device may be further reacted with another material at step 104 to produce a functionalised grafted polymeric product. At step 105 the selected grafting material is grafted onto the polymeric device, thus creating a material that has a functionally modified surface through another material being covalently attached. At step 106 the grafted polymeric product is sterilised for later use and at step 107 the said device is stored. At a later date the grafted device may be used in its given application. Thus for example if the selected device at step 101 was a blood oxygenator then after functionalisation at step 103 followed by grafting at step 105 the said device may be used at step 108. The invention is not limited to medical devices, but its application is particularly well suited to this application domain.

Figure 2:
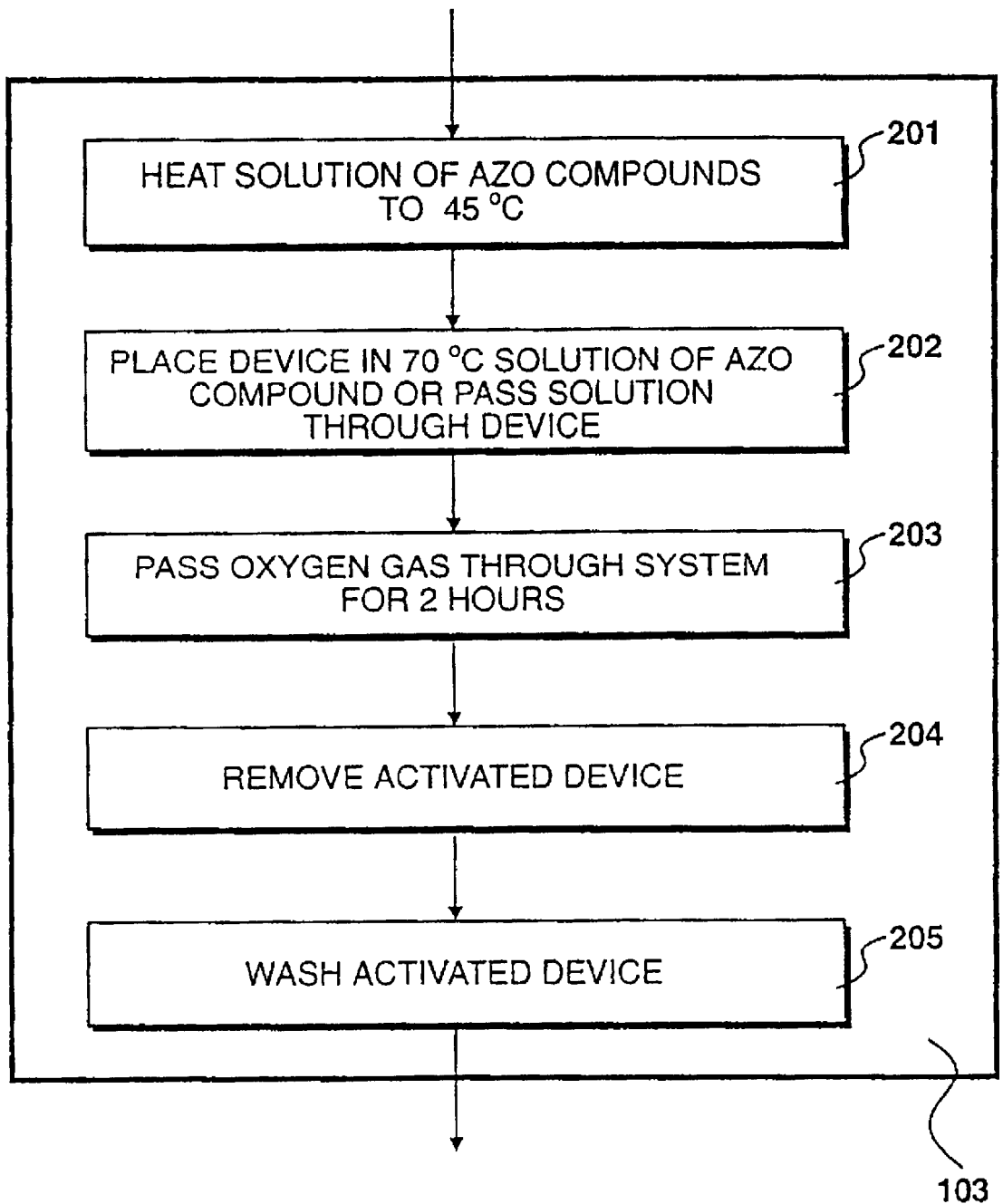
FIG. 2 details the device activation step identified in FIG. 1, including a step wherein oxygen gas is passed through the system.

Step 103 for activating a given polymeric material is detailed in FIG. 2. This step follows step 102 in FIG. 1 wherein the required activation chemicals have been selected. Thus at step 201 one or more azo compounds are heated to 70° centigrade. The said one or more azo compounds are water soluble and a suitable compound is 4,4'-azobis (cyanovaleric acid) or 2,2'-azobis (2-methyl propionamidine) dihydrochloride. At step 202 the device is placed in the solution of said one or more azo compounds heated in step 201. The device may not simply be placed in a solution of said compound, but rather could have said compounds pumped through its internal mechanism. Thus typically a blood oxygenator consists of an inlet pipe connected to the oxygenating mechanism which in turn is connected to an outlet pipe. This structure, an inlet means, an internal mechanism and an outlet means is typical of many devices used in the medical field which are concerned with blood flow. With the azo compound solution being circulated through the selected device, oxygen gas is passed through the azo compound solution for approximately two hours as indicated at step 203, while this process is proceeding. Having had sufficient time for the required functional groups substitution to have taken place to a sufficiently high degree the activated device is removed at step 204 whereafter at step 205 the activated device is washed with distilled water.

Figure 3:
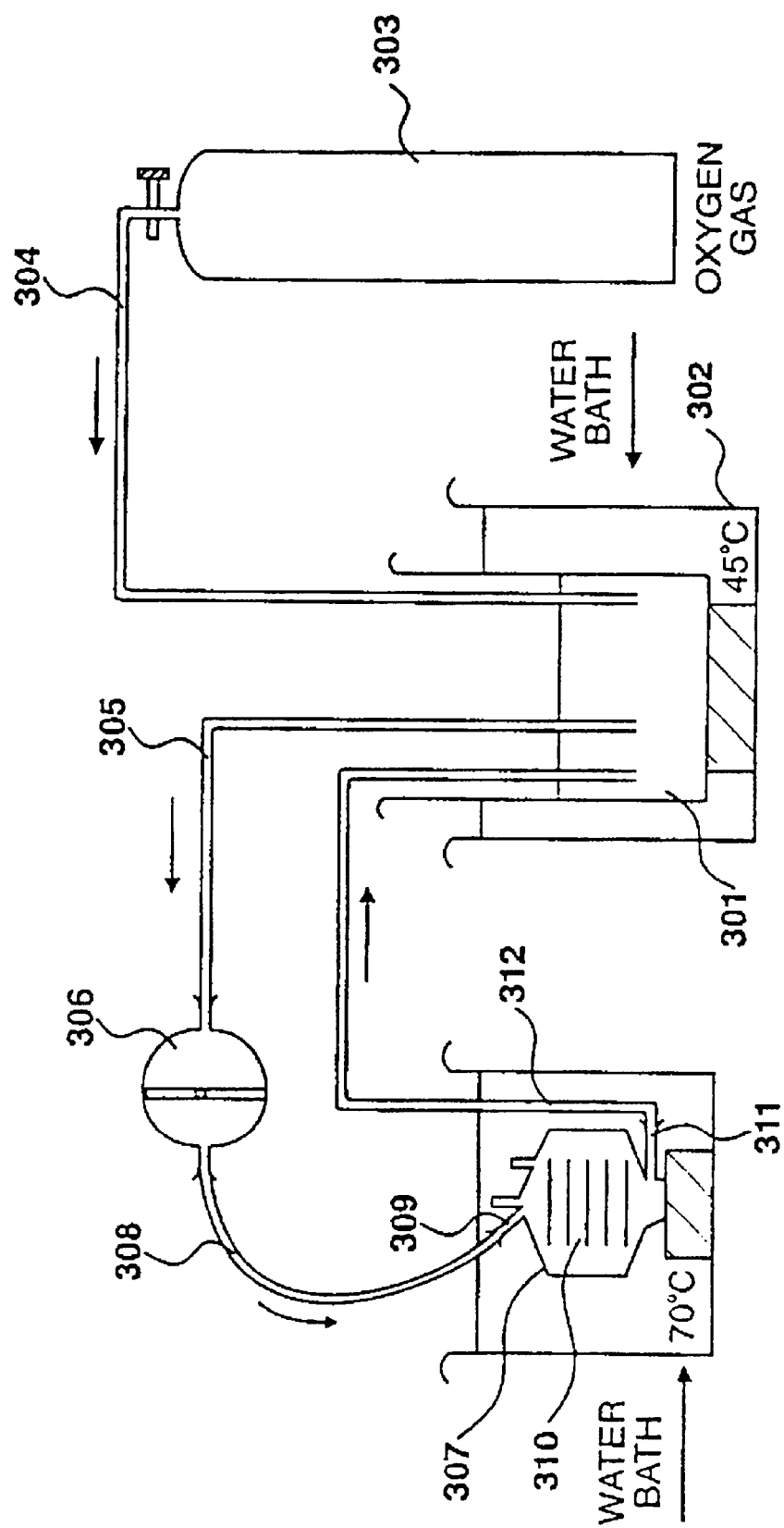
FIG. 3 details apparatus for undertaking the activation step identified in FIG. 1.

FIG. 3 shows a typical laboratory arrangement for undertaking the above activation procedure. A vessel 301 containing the selected azo compound solution is placed in a water bath 302 which is maintained at a preferred temperature of approximately 45° centigrade. Oxygen gas is supplied from cylinder 303 via tube 304 into the azo compound solution. It is sufficient to allow a steady stream of oxygen bubbles to emanate from the terminal orifice of said tube 304. Thus the oxygen gas is released at substantially very low pressure. The azo compound solution is drawn up through tube 305 by the peristaltic pump 306. In practice the peristaltic pump 306 will be located on the bench surface next to one of the water baths such as water bath 302. On leaving the peristaltic pump 306 the azo compound solution is directed to the polymeric device 307 via pump outlet tube 308. The polymeric device is positioned in a water bath having a temperature of 70° C. Outlet tube 308 is connected to polymeric device 307 via inlet 309. Thus azo compound solution passes into polymeric device 307 wherein said solution passes through the internal mechanism 310 of said device. In doing so said azo compound solution activates the surface of internal mechanism 310. Having passed through the internal mechanism 310 of the device 307, the azo compound solution exits said device via outlet 311 wherein said solution passes back, via connecting tube 312, to vessel 301. Thus a cyclical process is maintained by peristaltic pump 306, in effect recycling the azo compound solution through the device 307 until the surface of internal mechanism 310 is sufficiently activated. In the system shown, activation pertains to hydroxylation of said surface, said hydroxylation being the appropriate functionalisation in respect of use of oxygen gas and one or more azo compounds.

The above system shown in FIG. 3 could be scaled up to industrial proportions, possibly having several cyclical mechanisms for flow of azo compounds wherein a given polymeric device is attached to each of said cyclical flow systems.

Figure 4:
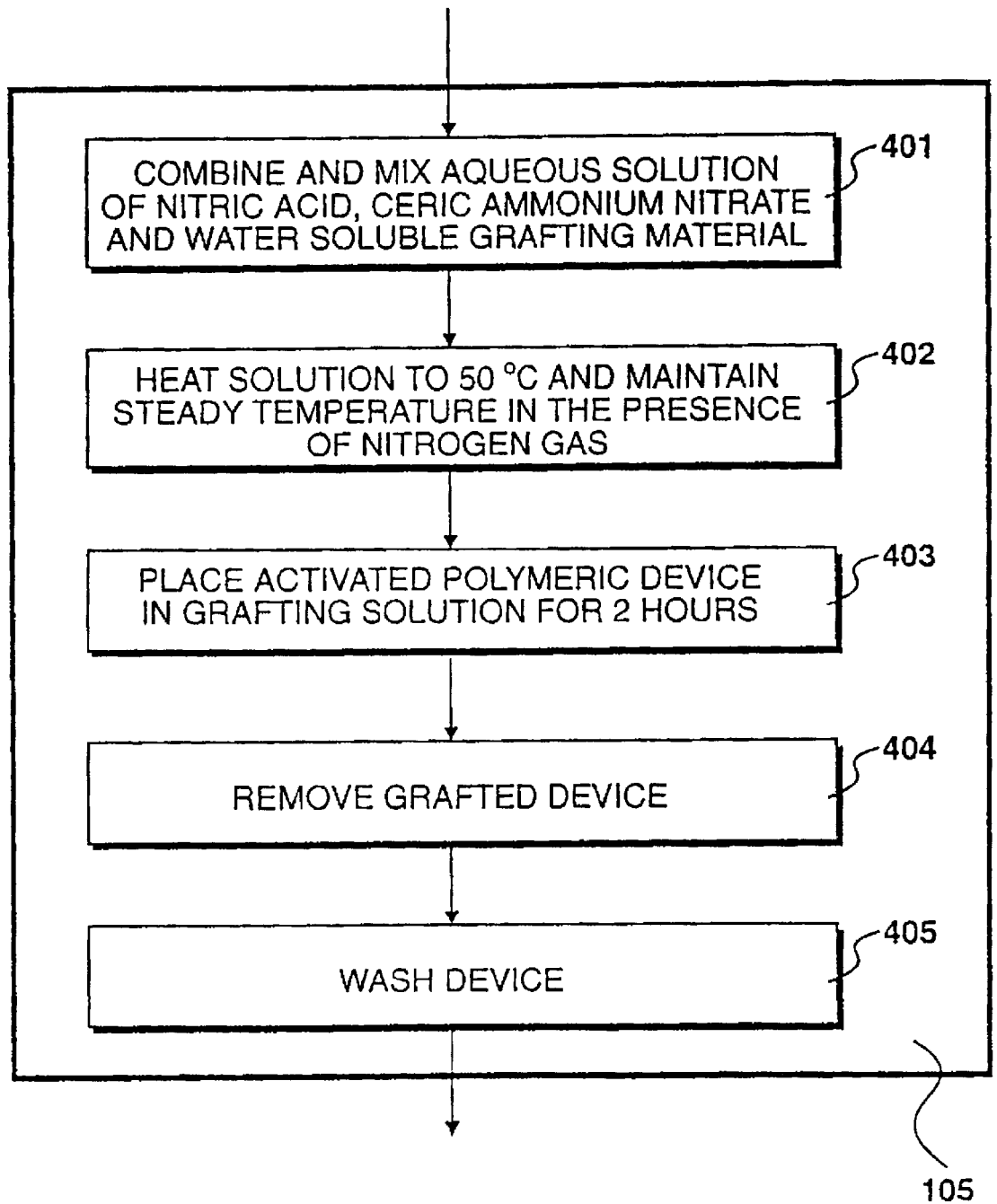
FIG. 4 details the grafting step identified in FIG. 1.

FIG. 4 details the further process of grafting an additional material onto a selected substituted polymeric material, indicated generally at step 105 in FIG. 1. This follows step 104 wherein a suitable grafting material together with appropriate chemicals to facilitate grafting are selected. At step 401 the selected chemicals used to facilitate grafting are mixed and combined with a selected grafting material. A suitable grafting material could be for example a water soluble vinyl monomer such as acrylamide or a water soluble biomolecular species such as Heparin macromer. Chemical facilitants include nitric acid, ceric ammonium nitrate and water. Use of these chemicals to graft one material onto another is generally referred to as the ceric ion technique. Once mixed sufficiently by simple stirring, the combined solution is heated to approximately 50° centigrade and maintained at a steady temperature in the presence of nitrogen gas as indicated in step 402. Once a steady temperature is maintained a selected activated polymeric device is placed in said solution for approximately two hours as indicated at step 403. As with the substitution process described above the polymeric device may not be placed in the said solution, but rather will have the said solution passed through its internal mechanism, thus grafting material onto its internal mechanism surface. Once grafting has been achieved to a sufficient degree the processed device is removed from the apparatus as indicated at step 404, whereafter the given device is washed with distilled water at step 405.

Figure 5:
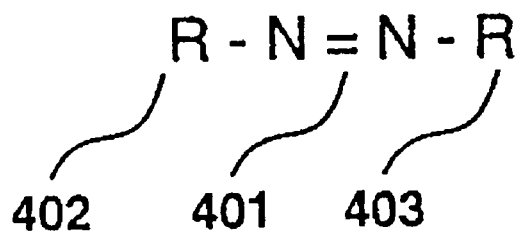
FIG. 5 details the general formula for an azo compound.

FIG. 5 illustrates the general formula for an azo compound wherein it is observed that an azo compound is defined by having a double covalent bond 501 between two nitrogen atoms. Connected to each nitrogen atom is a general group or chain ® 502 and 503 respectively. Groups 502 and 503 may either be different chemical groups or the same chemical groups.

Figure 6:
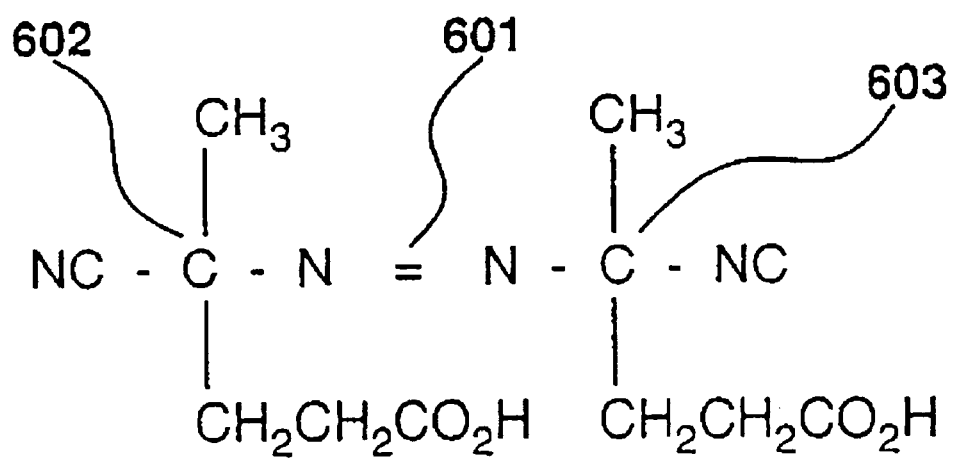
FIG. 6 details a preferred azo compound as used in the present invention.

FIG. 6 illustrates the general structure of a suitable azo compound, as used in the preferred embodiment. A double bond 601 is present between the two cental nitrogen atoms. This chemical is symmetrical in that each chain attached to each central nitrogen atom has the same chemical structure. The chemical structure of the attached chains comprises a central carbon atom with a methyl group connected, a dimetylcarboxy group connected and said chain terminating in another carbon atom connected to a nitrogen atom, said carbon and nitrogen atoms being connected via a treble covalent bond. The azo compound used in the preferred embodiment is known by the commercial name 4,4'-Azobis (4-cyanovalerc acid) as supplied by Aldrich Chemical Company. In general any water soluble azo compound or mixture of water soluble azo compounds capable of producing free radicals may be suitable for use in the present invention.

Figure 7:
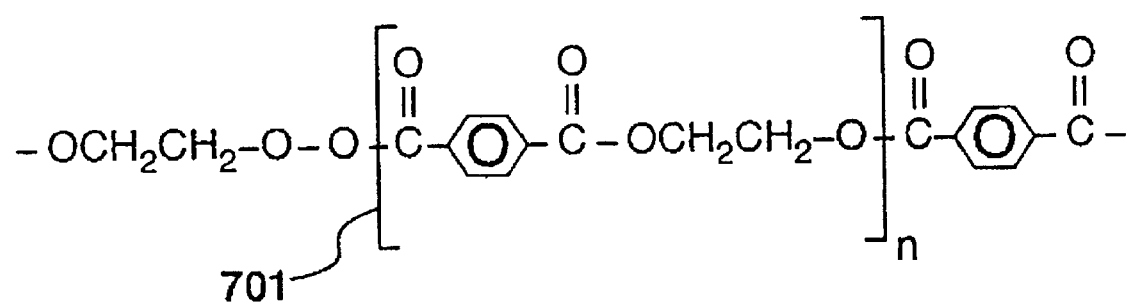
FIG. 7 details the chemical structure of a polymeric material suitable for substitution of functional groups, according to the present invention, said polymer being polyethylene terephthalate (Terylene).

FIG. 7 illustrates a typical polymeric material that may be required to be functionalised in accordance with the present invention. The repeating monomer of this polymer is enclosed in braces 701. This particular polymer is a polyester known as poly(ethyleneterephthalate), commonly known as Terylene. In general many types of polymeric material may be activated by functional group substitution, in accordance with the present invention. Typical polymeric materials which may be functionalised via functional group substitution as described above, include olefin polymers, polyurethanes, polyesters, polyamides, polyvinylchloride polymers, polysulphons or polymers containing aromatic rings for example.

Figure 8:
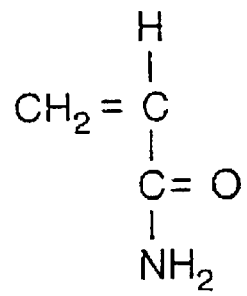
FIG. 8 details an acylamide monomer, suitable for grafting onto a polymeric material.
Figure 9:
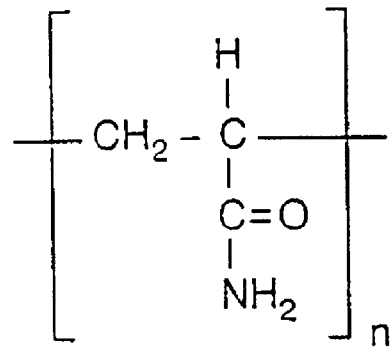
FIG. 9 details the polymer, Polyacrylamide formed from polymerisation of monomers of the type detailed in FIG. 8.

FIG. 8 illustrates the chemical structure of an acrylamide monomer and FIG. 9 illustrates the structure of polyacrylamide, formed from polymerisation of the monomers detailed in FIG. 8.

The present invention will be further described with reference to the use of azo compounds as the active agent initiating free radical formation, and oxygen being the chemical species used to facilitate said reactions. The reactions are described with respect to the azo compound 4,4'-azobis (cyanovaleric acid). The reactions are not limited to use of one azo compound and a plurality may be used. Thus for example a combination of 4,4'-azobis (cyanovaleric acid) and 2,2'-azobis (2-methylpropionamidine) dihydrochloride may be used.

Figure 10:
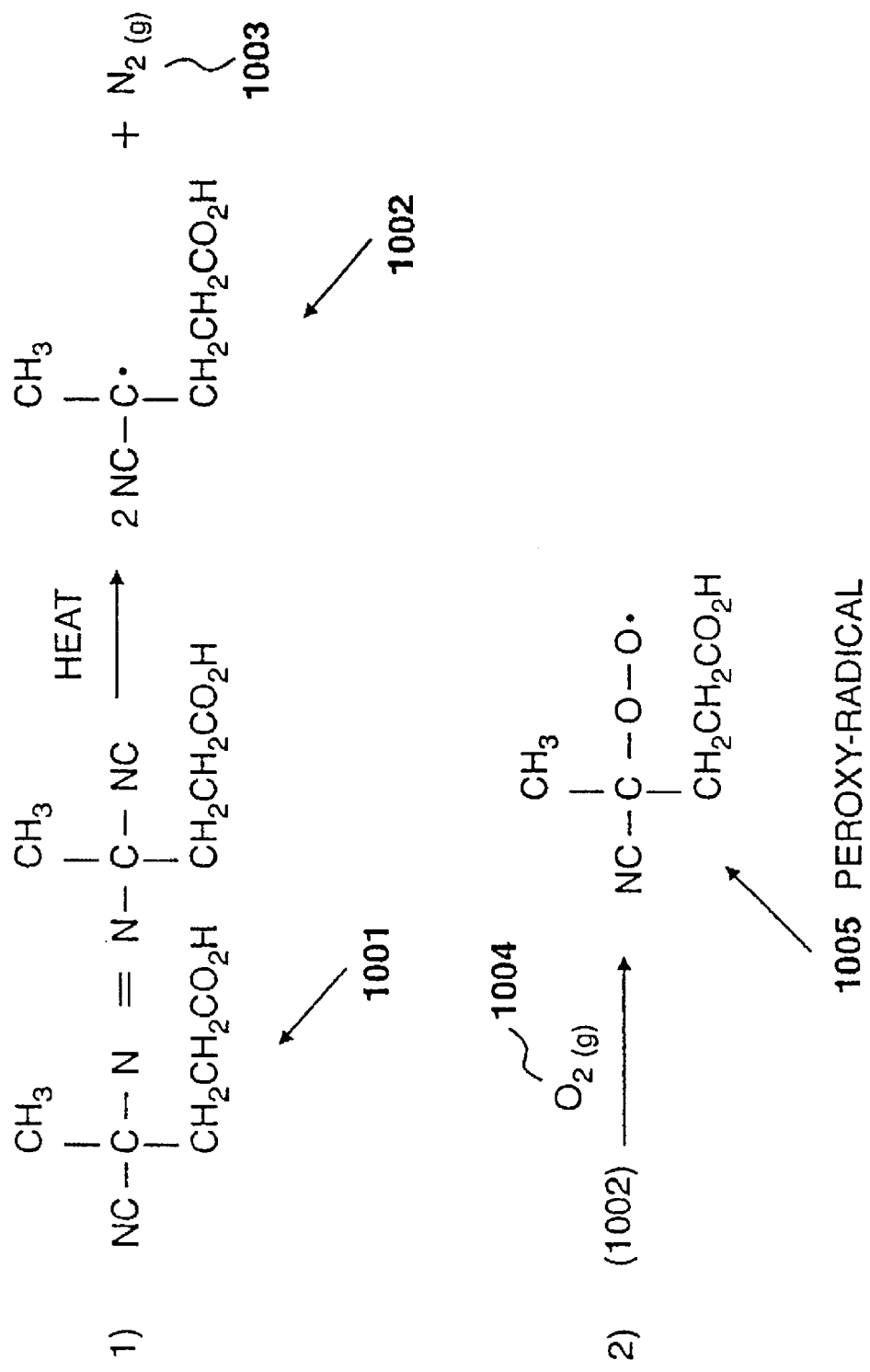
FIG. 10 details reaction of the azo compound detailed in FIG. 6, with oxygen gas, resulting in formation of chemical radicals.

Thermal decomposition of the selected water soluble azo compound is detailed in reaction (1) shown in FIG. 10. The degree of decomposition depends on the temperature and the preferred temperature is approximately 70° centigrade. The range of temperatures preferred for these reactions, and the accompanying reactions described below, lie between 40° centigrade to 100° centigrade. Alternatively the reactions may be conducted photochemically, the wavelength of light used being between 300 nm to 600 nm. These temperatures or photochemical conditions are found to give a sufficient yield of required hydroxyl free radicals to provide a substitution medium that operates on a selected polymeric material in a realistic time scale. Azo compounds tend to be sensitive to decomposition via thermal or photochemical means. Because of this the azo compounds used in the present invention must be stored in a fridge to reduce decomposition processes, before being applied in the substitution process. Decomposition of the azo compound 1001 is seen to yield two free radicals 1002 together with nitrogen gas 1003. The second reaction in FIG. 10 details reaction of free radicals 1002 with oxygen gas 1004 to yield a peroxy-radical, 1005. Thus for each molecule of azo compound 1001 two peroxy-radicals 1005 are formed.

Figure 11A:
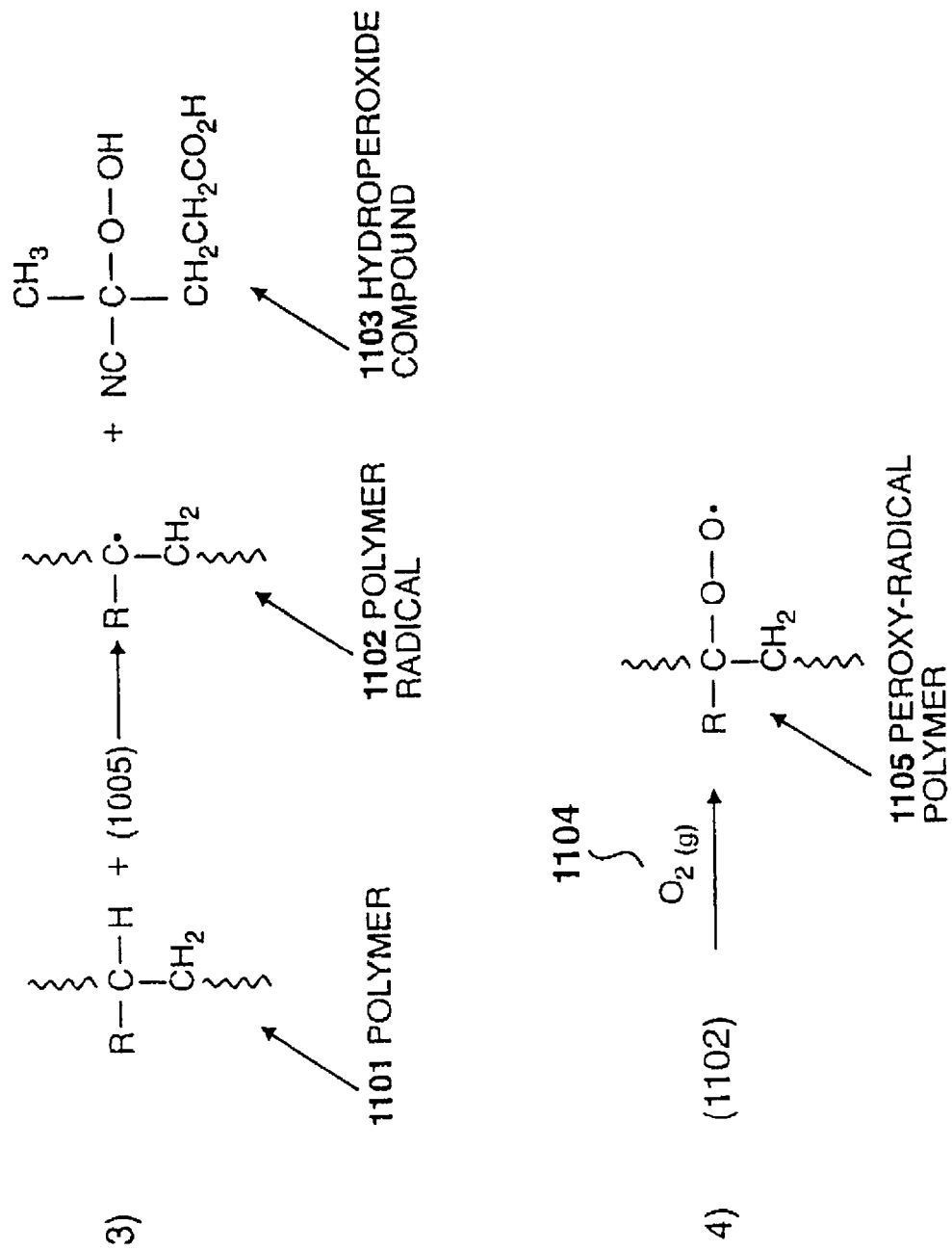
FIGS. 11A and 11B detail further steps in the reaction mechanism, said reactions substantially pertaining to reaction of a given polymeric material.
Figure 11B:
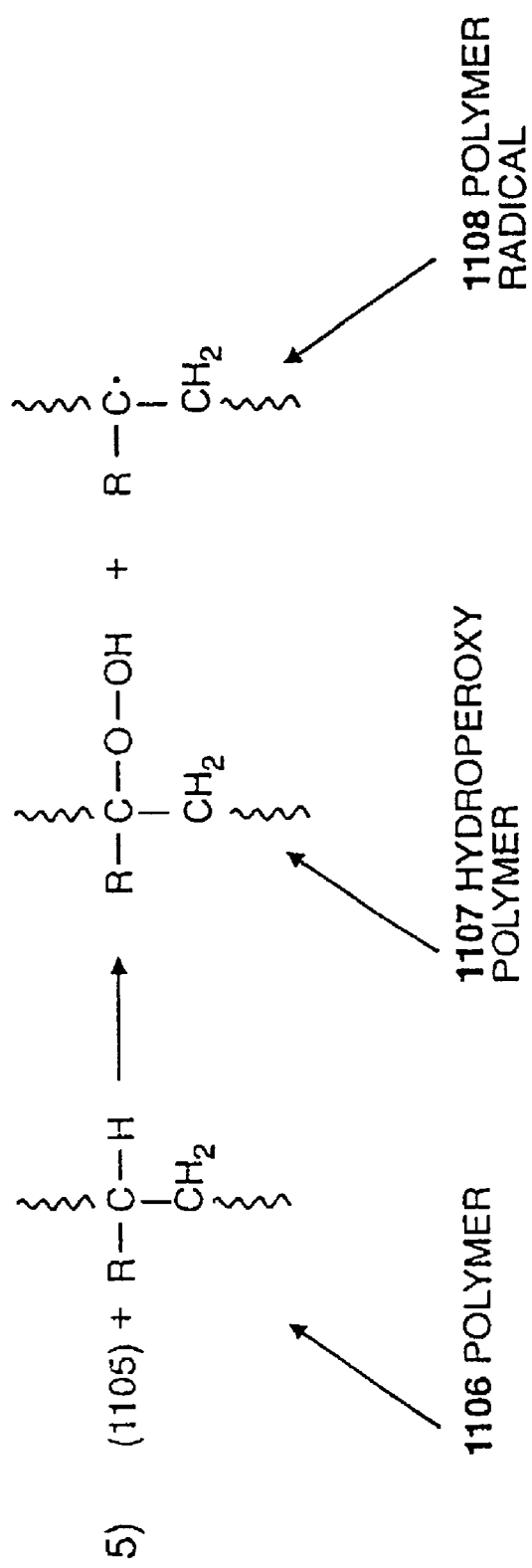
Figure 12:
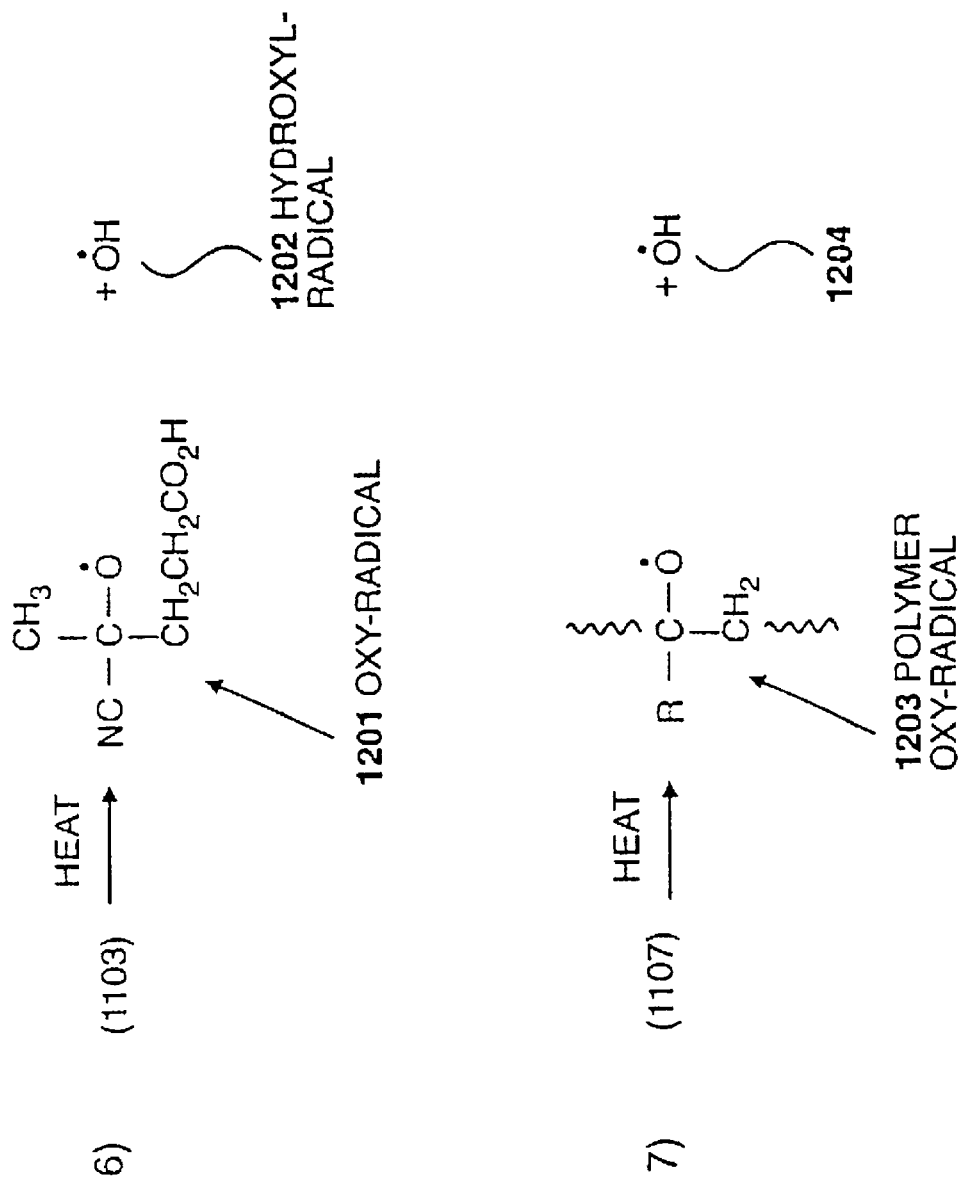
FIG. 12 details further steps in the reaction mechanism wherein hydroxyl radicals are produced.

FIGS. 11A and 11B detail further reactions involved in the thermal process. A polymer, 1101 is shown which is selected from store as detailed in FIG. 1 at step 101. As described earlier this polymer may be in the form of a device such as for example a blood oxygenator. The polymer reacts with the peroxy-radicals (1005) formed in reaction (2) of FIG. 10 to produce polymer-radicals 1102 and a hydroperoxide compound, 1103. The reaction conditions, such as temperature and time, can be selected in accordance with the degree of functional group substitution required. Thus in certain applications, as in the case of the preferred embodiment, said conditions are chosen such that not all the surface polymers are substituted. Reaction (4) shows the polymer radical, formed in reaction (3), reacted with oxygen gas 1104 to produce a peroxy-radical polymer 1105. Reaction (5) details reaction of the peroxy-radical polymer, 1105 with the polymer 1106 to produce a hydroperoxy polymer 1107 and a further free polymer radical 1108. The hydroperoxy polymer 1107, in general is a minor product, the amount of said product depending for example on the temperature of reaction and the time allowed for the reactions to take place. Reaction (6) in FIG. 12 details thermal decomposition of the hydroperoxide compound 1103 and reaction (7) details the thermal decomposition of the hydroperoxy polymer 1107. In the former case an oxy-radical 1201 is formed together with a hydroxyl radical, 1202. Similarly reaction (7) produces a polymer oxy-radical 1203 and a hydroxyl radical 1204. As described above for the earlier reactions these reactions may proceed via a photochemical process rather than a thermal process.

Figure 13A:
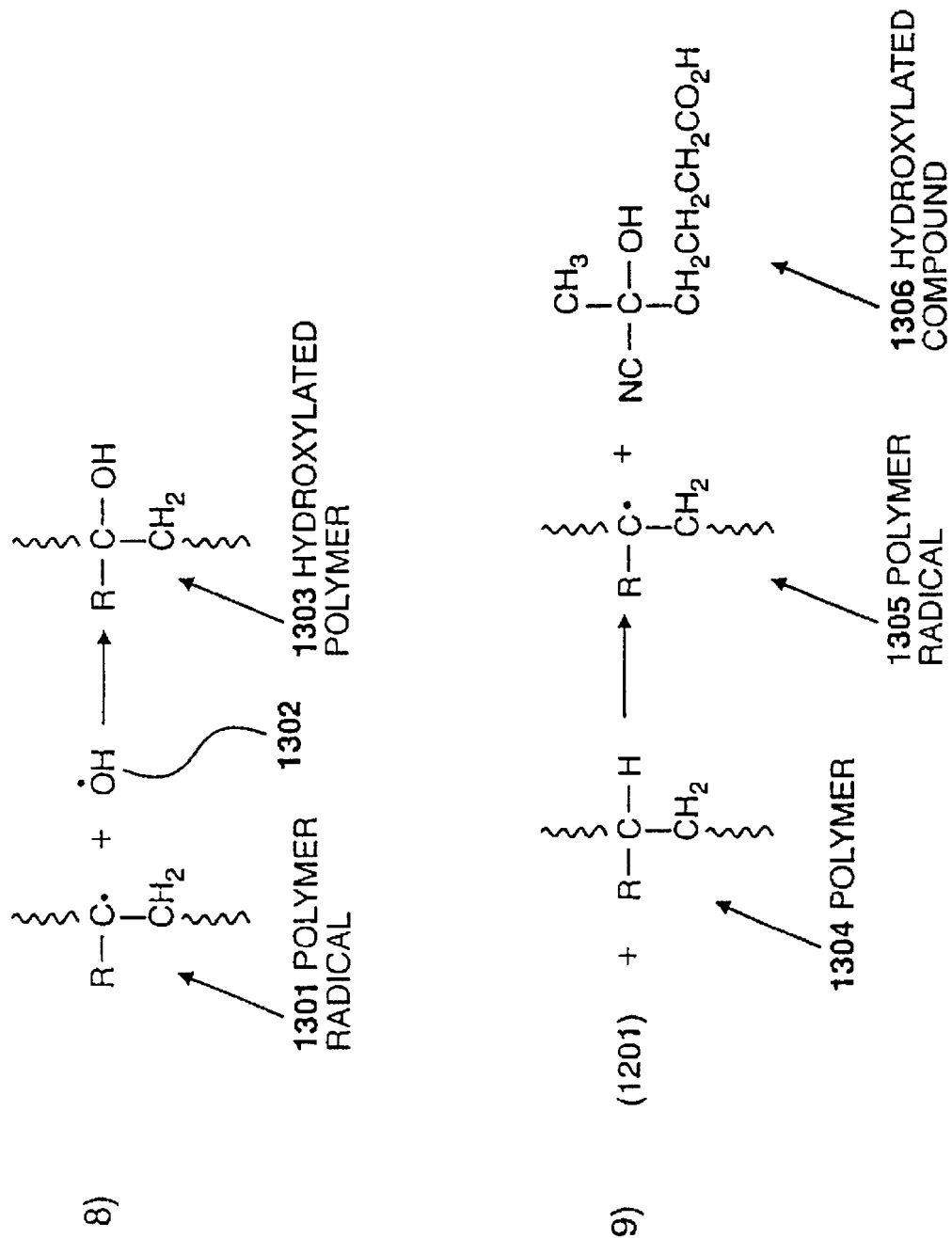
FIGS. 13A and 13B detail further steps in the reaction mechanism, said steps substantially pertaining to formation of a hydroxylated selected polymer.
Figure 13B:
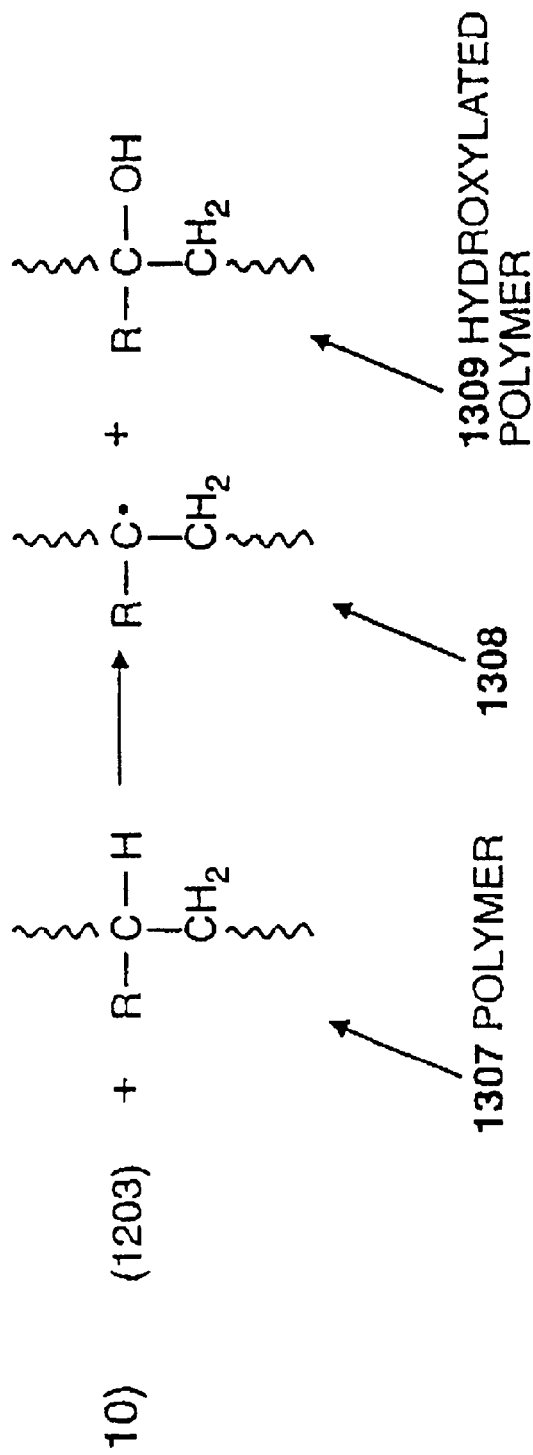

FIGS. 13A and 13B detail three further chemical reactions, labelled (8), (9) and (10) respectively. Reaction (8) details a polymer-radical 1301 formed in either reactions (3) or (5), reacting with a hydroxyl radical 1302 formed in reaction (6) or (7), to produce a hydroxylated polymer (a substituted polymer) 1303. Reaction (9), the second reaction in FIG. 13 details reaction of the oxy-radical 1201 (formed in reaction (6)) with a polymer 1304 to produce a polymer-radical 1305 and a hydroxylated compound 1306. Similarly reaction (10), details reaction of the polymer oxy-radical, 1203 (formed in reaction (7)) with a polymer 1307 to produce a polymer radical 1308 together with a hydroxylated polymer (substituted polymer) 1309.

Thus reactions (8) and (10) are the final stages involved in the formation of a hydroxylated polymer. This mechanism pertains only to use of oxygen gas and azo compounds facilitating hydroxylation. Other forms of substitution may be undertaken in a similar manner using a different active agent and a different chemical species. From the above reactions it is clear that for a given molecule of azo compound a plurality of hydroxyl free radicals are produced. In the mechanism outlined above the number of hydroxyl free radicals produced, for a given molecule of azo compound is four. It is also dear that hydroxyl free radicals are produced in addition to formation of a hydroperoxy polymer and also a hydroperoxide compound, the latter derived from the azo compound. As described in FIG. 2 the above reactions proceed for two hours in the preferred embodiment, resulting in a polymer that is substituted. In the case of the mechanism above the said polymer is substituted with hydroxyl radicals to produce a hydroxylated polymer. Such hydroxylated polymers are known to be suitable for further processing, such as for example, grafting materials onto the parent polymer.

Figure 14:
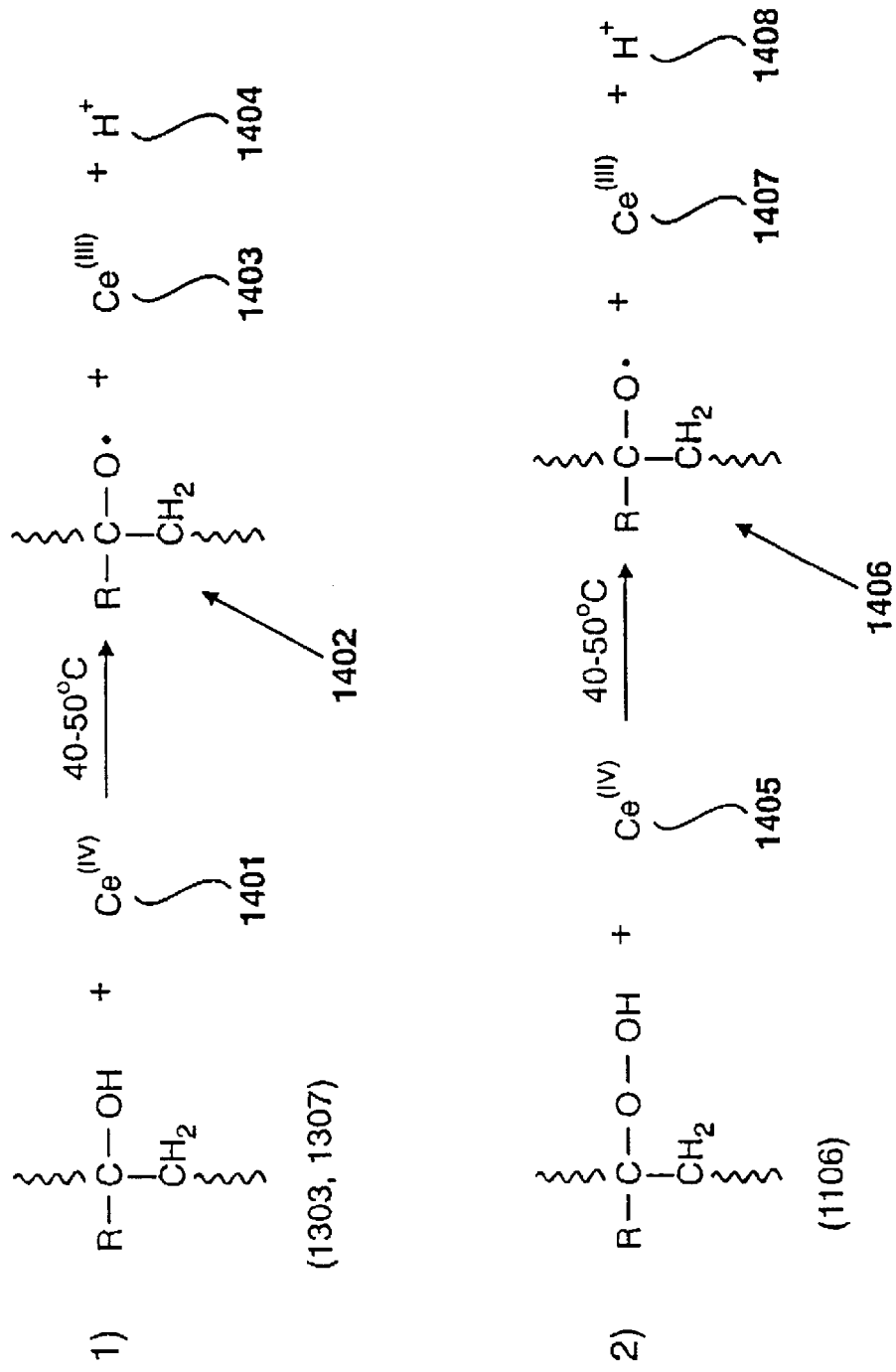
FIG. 14 details further reaction of a substituted polymer, as formed in FIGS. 11 and 13, with ceric (IV) ions.

FIG. 14 details thermal reactions of the hydroxylated polymer, 1303 and 1307, with ceric ions 1401 in reaction (1) of the Figure. This reaction is conducted between 40 to 50° centigrade and produces an oxy-radical 1402 along with a ceric (III) ion 1403 and a hydrogen ion 1404. Reaction (2)

in FIG. 14 details reaction of the hydro-peroxy polymer 1106 with a ceric (IV) ion 1405, to produce an oxypolymer radical 1406 together with a ceric (III) ion 1407 and a hydrogen ion 1408. Again this second reaction is ideally conducted at a temperature of between 40 to 50° centigrade in the preferred embodiment.

Figure 15:
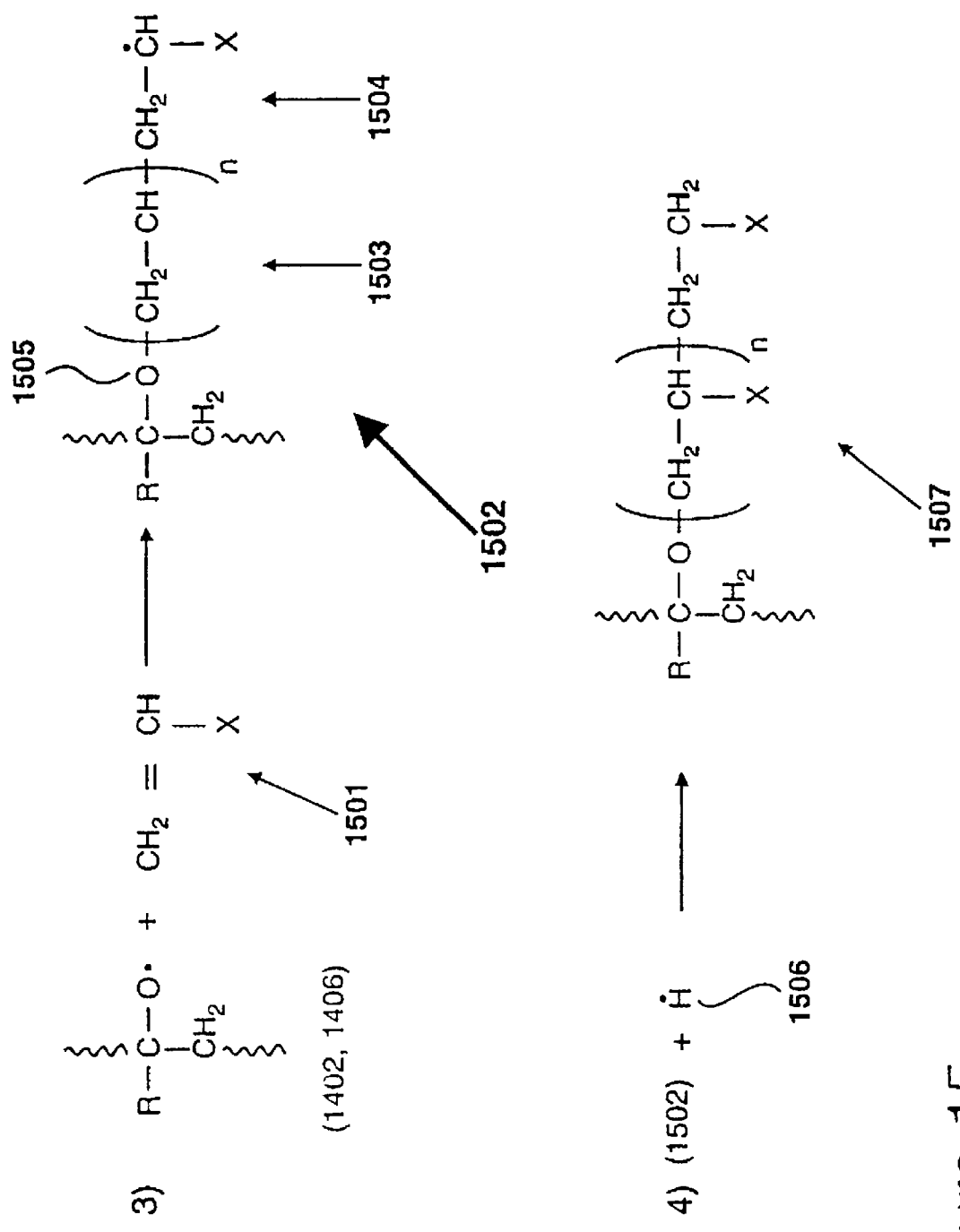
FIG. 15 details further steps wherein the products detailed in FIG. 14 are further reacted with a suitable grafting material, resulting in a grafted functionalised polymeric material.

FIG. 15 details two further reactions wherein a selected grafting material 1501 is reacted with a polymer oxyradical (1402 or 1406), produced in FIG. 14. In this Figure the selected grafting material is a vinyl monomer such as for example acrylamide. Due to the nature of the reactions a water soluble grafting material is preferred to the grafting process. As illustrated, the vinyl monomer 1501 reacts with the polymer oxyradical to produce a polymer 1502, associated with the medical device, that is covalently bonded to a chain of linked vinyl monomers 1503, said linked chain eventually terminating in the free radical terminal group 1504. Thus this diagram illustrates a selected polymeric material with a functionalised surface (the oxygen atom 1505) bonded to a chain of grafted material 1503. The grafted material derived from monomeric material is built up as the reaction proceeds, a monomer being added onto the last one added, in succession. Eventually on termination of the reaction the final monomer added to the grafted polymeric chain reacts with for example a hydrogen radical abstracted from a polymer chain by chain transfer so as to produce a polymeric chain that is stable. The second reaction in FIG. 15 illustrates this termination process, the grafted polymeric material (end group 1504) of 1502 reacting with a hydrogen radical 1506 to produce a stable grafted polymeric material 1507.

In all applications it is essential to perform the grafting reactions such as those shown in FIGS. 14 and 15, in the presence of nitrogen gas. Specifically, some medical devices such as a blood oxygenator have micropores in the polymeric material that may become blocked during grafting. The presence of nitrogen gas aids in the prevention of said pores becoming blocked. In the embodiment described it is sufficient to have a steady stream of nitrogen gas passing through the system during the grafting process. The grafting process detailed in FIGS. 14 and 15 produces a functionalised grafted polymeric product. The grafting material may be a vinyl monomer such as for example N,N-dimethylacrylamide or acrylamide or 3-amino propylmethacrylamide, or it may be a macromer of a biomolecular species such as Heparin, Hirudin, or any other drugs. In the case where the grafting material is a vinyl monomer, the resulting functionalised polymeric grafted material may be further treated by attachment of a biomolecular species such as one of the biomolecules mentioned above. Thus in effect a biomolecular species may be grafted directly onto the functonalised polymer or a biomolecular species may be added at a later stage, following initial grafting with a non biomolecular species. In all cases the final functionalised and grafted polymeric material must be sterilised before further use, this being particularly important in devices used in medical applications.

As indicated in the above reaction mechanisms both hydroxy and peroxy polymers are produced. A peroxy polymer is produced as a minor product in the embodiment described. However, it may be that conditions can be varied such that these products take on a more significant role. In such cases it may be preferable that both peroxy and hydroxy produced polymers are processed through grafting as described above.

Figure 16:
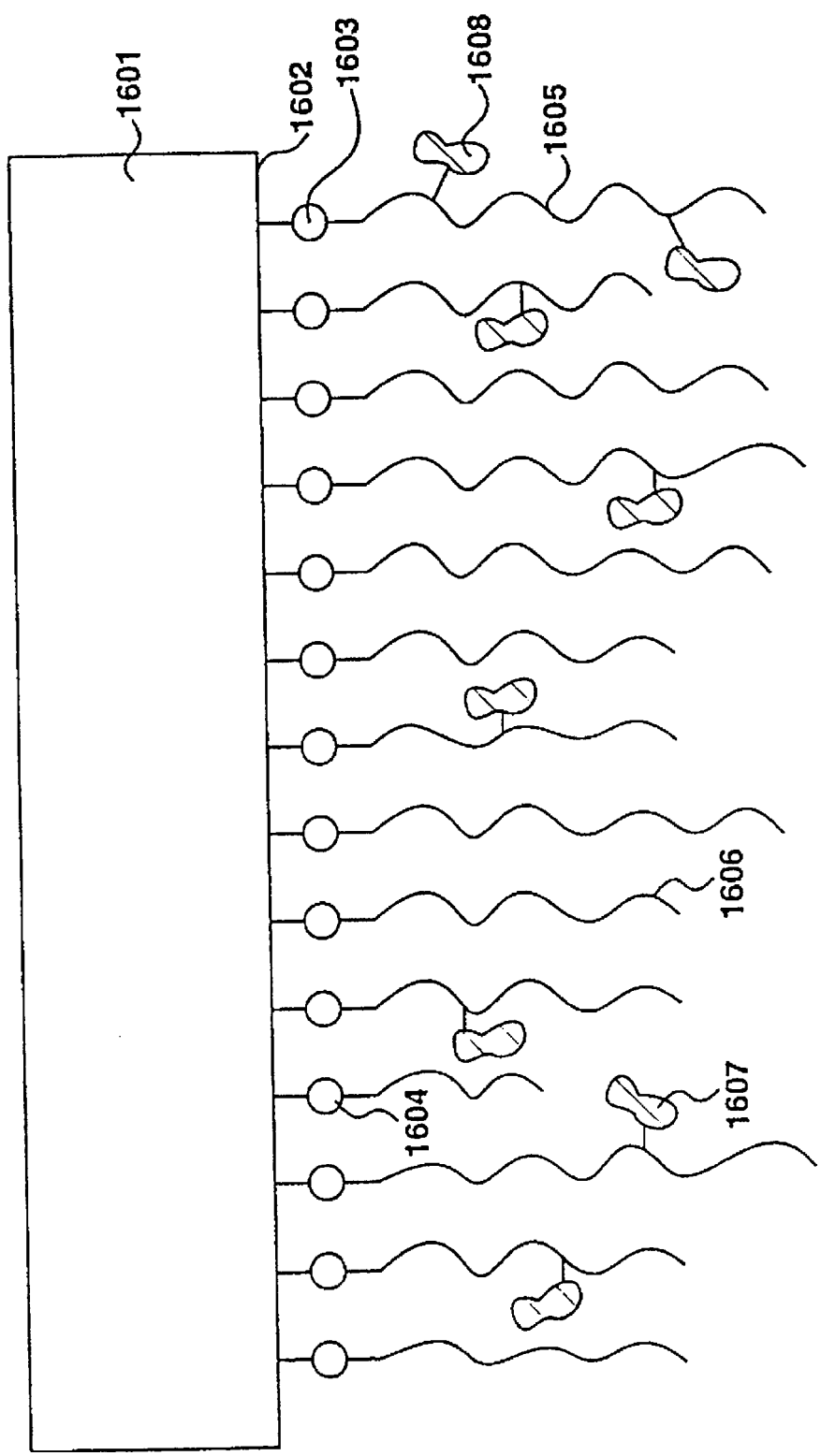
FIG. 16 generally illustrates a functionalised polymeric material having grafted polymers together with incorporated bio-molecular species chemically bonded to its surface.

FIG. 16 illustrates a general polymeric material 1601, such as material forming a blood oxygenator, with a functionalised surface 1602 produced in accordance with the preferred embodiment described. A functionalised surface therefore consists of covalently bonded oxygen atoms, 1603 and 1604 for example. Two of said covalently bonded oxygen atoms have grafted polymers 1605 and 1606 respectively. These grafted polymers are shown as having varying lengths, the lengths depending on random conditions involved during the reaction, said conditions pertaining to each individual grafted polymer chain. Further illustrated, are attached biomolecular species 1607 and 1608 for example. These species are, for example, typically anticoagulants. The biomolecular species may be attached at varying positions along the grafted polymeric chains, and it may be desirable to position said biomolecules at certain positions along said chains. Thus this diagram pertains to a polymeric material grafted with a non biomolecular grafting material, said non biomolecular grafting material being further modified by attachment of biomolecular species. The grafted polymeric chains preferably have certain other properties such as for example being hydrophilic or hydrophobic. In a preferred embodiment the monomeric material used to form grafted polymers from the selected polymeric material, is selected such that the grafted polymers are hydrophilic in nature. Thus when a polymeric device is treated by the above processes the grafted surface, being hydrophilic, becomes slippery due to water molecules being attracted to its surface. This aids in the reduction of problems arising with blood flow through a medical device. Such problems include for example blood coagulation, cell and protein deposition and so on. In certain applications it may be preferable to graft materials which result in a grafted polymeric product having a hydrophobic surface.

Figure 17:
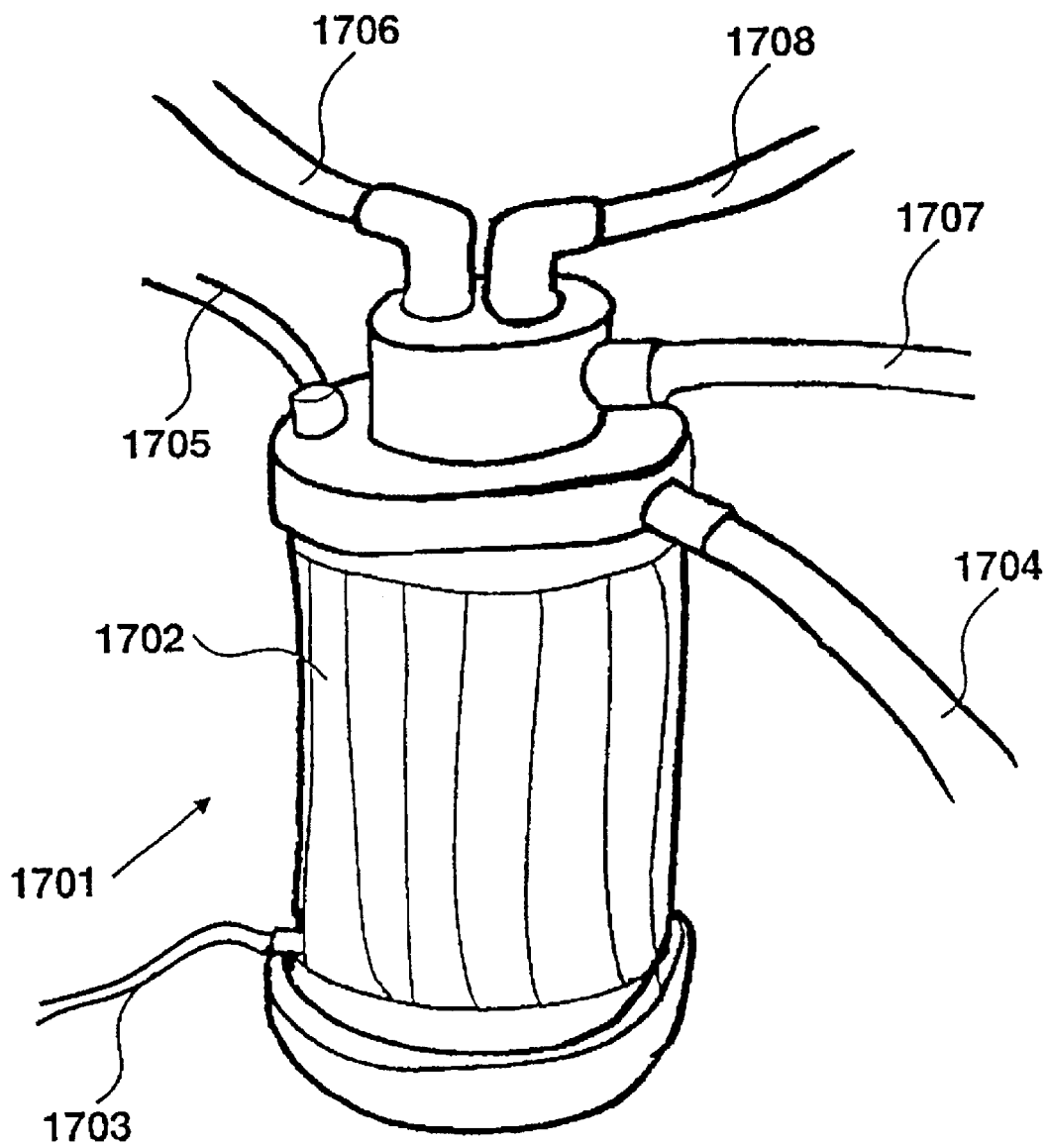
FIG. 17 illustrates a typical polymeric device in which the functionalisation process and grafting process may be used, said device being a blood oxygenator.

FIG. 17 illustrates a typical blood oxygenator 1701, as used in many hospitals. A hollow fibre portion, 1702 is shown and an infusion inlet 1703 is provided. Blood flows into the device through inlet pipe 1704 and oxygen is supplied through inlet pipe 1705. Similarly water enters through inlet 1706. Oxygenated blood exits the device through outlet 1707 and water exits via outlet 1708. This is a typical device that can be functionalised and grafted in accordance with the present invention. However the invention is not limited to such a device and many medical devices and polymeric materials will be suitable for treatment by the processes described. Examples include contact lenses, catheters, vascular prostheses, blood oxygenators, blood filters, haemodialysers, blood containers, surgical equipment and surgical tools, artificial cardiovascular devices such as heart valves or any other medical devices.

The present invention is further illustrated by the following examples of laboratory scale synthesis.

EXAMPLE 1

(a) Hydroxylation of Polymeric Materials

Different types and forms of polymeric materials were heated at 60° C. in an aqueous solution of 1% w/v 4,4'-azobis (4-cyanovalerc acid) for 2 hours. During the process, a stream of oxygen gas was passed through the solution continuously. The samples were then washed with water before being subjected to grafting.

(b) Grafting of Hydroxylated Polymeric Materials

The hydroxylated polymers produced in stage (a) were then grafted with an aqueous solution of 10% w/v acrylamide containing 0.04M nitric acid and 0.005M ceric ammonium nitrate at 50° C. for 2 hours. The grafted samples were then washed with water. Samples treated as described above are listed in the table below, with a general indication of the degree of hydrophilicity produced being provided:

| Polymer | Type | Degree of Hydrophilicity |
| --- | --- | --- |
| Polyamide (Example; Nylon 12) | Catheter | Very slippery |
| Polyamide (Example; Nylon 12) | Film | Very slippery |
| Polycarbonate | Connector | Very slippery |
| Polyester (Example; Poly-ethylene-terephthalate) | Membrane | Very slippery |
| Polyester (Example; Poly-ethylene-terephthalate) | Film | Very slippery |
| Polypropylene | Hollow fibres | Very slippery |
| Polystyrene | Film | Slippery |
| Polyurethane (Example; Aliphatic) | Catheter | Very slippery |
| Polyurethane (Example; Aliphatic) | Film | Very slippery |
| Polyurethane (Example; Aromatic) | Catheter | Very slippery |
| Polyurethane (Example; Aromatic) | Film | Very slippery |
| Polyvinylchloride | Tube | Slippery |

EXAMPLE 2

(a) Hydroxylation of Polymeric Materials

Samples of high density polyethylene (HDPE), polyamide 12 (PA 12) and silicone rubber were heated at 70° C. with 1% w/v of 4,4'-azobis (4-cyanovaleric acid) for 3 hours. During the process, a stream of oxygen gas was passed through the solution continuously. The samples were then washed carefully with water before being submitted to the grafting process.

(b) Grafting of Hydroxylated Polymeric Materials

The hydroxylated samples were placed in an aqueous solution containing 10% w/v acrylamide, 0.1% w/v ceric ammonium nitrate and 2 ml of nitric acid (1N). The reaction was carried out at 50° C., in the presence of a continuous stream of nitrogen gas for 1 hour. The grafted samples were then washed carefully with water and dried to achieve constant weight.

The table below shows the degree of grafting onto the polymeric samples.

| Sample | % Grafting |
| --- | --- |
| HDPE | 6.3 |
| PA 12 | 8.3 |
| Silicone Rubber | 1.0 |

In the above table the percentage grafting represents the percentage of material grafted onto a polymeric material as a percentage of the total weight of the grafted material and the polymeric material combined.

EXAMPLE 3

(a) Hydroxylation of Polymeric Materials

A sample of poly(ethyleneterephthalate) (PET) was reacted with one percent 4,4'-azobis (4-cyanovaleric acid) in the presence of a stream of oxygen gas for 3 hours at 70° C. The sample was then washed carefully with water before being reacted further.

(b) Grafting of Hydroxylated Polymeric Materials

The hydroxylated PET sample was placed in an aqueous solution containing 10% w/v acrylamide, 0.1% w/v N-(3-amino propyl) methacrylamide hydrochloride and 0.1% w/v ceric ammonium nitrate solution containing 2% v/v nitric acid (1N). The grafting was carried out for 3 hours at 50° C. in the presence of nitrogen gas and was then washed carefully with hot water. The grafted PET was very slippery and gave positive Eosin Y test result. This test confirms the presence of amino groups on the surface of the hydroxylated PET.

(c) Attachment of Biomolecular Species (Heparin Coupling)

The Grafted PET sample was reacted with 0.1% w/v Heparin. This was facilitated via the use of a coupling agent, said coupling agent being 1-ethyl-3-(-3-dimethyl amino propyl) carbodimide hydrochloride (pH 4–5) for 8 hours at room temperature. The sample was then carefully washed with water and sodium hydrogen carbonate (pH 9) respectively.

(d) Activated Partial Thromboplastin Time-FS (APTT-FS)

The APTT test has been widely used to monitor the effectiveness of Heparin therapy, where the clotting time is prolonged in proportion to the amount of Heparin used. In the test, a small sample of PET coupled with Heparin was placed in a test tube containing 200 micro liters of plasma and incubated for 1 minute at 37° C. Specifically the size of the PET sample used was 4 mm by 4 mm. Following incubation, 200 micro liters of APTT-FS agent were added into the test tube containing the plasma and the test sample, and then incubated for a further 3 minutes at 37° C. Following this incubation period, 200 micro liters of calcium chloride solution (20 mM) were added into the reaction mixture and simultaneously the timer was started and the clotting time recorded. The APTT results are shown in the table below:

| Sample | Mean Value of Clotting Time (Seconds) |
| --- | --- |
| Plasma | 35 |
| Control sample of Untreated PET | 14 |
| Test sample of PET coupled with Heparin | 60 |

Heparin increases the clotting time of blood. It acts as a catalyst to deactivate coagulation factors in the blood. Thus the above results indicate that untreated plasma takes longer to dot than plasma containing an untreated sample of PET. This indicates that the presence of PET reduces clotting time and gives a strong indication of the non biocompatibility of this material with plasma. However the third line of the above table, pertaining to the treated PET sample coupled with Heparin, clearly has a longer clotting time than either the pure plasma sample or the plasma sample containing untreated PET. These results indicate that a PET sample treated in accordance with the methods of the present invention pertaining to substitution, grafting of a non bio-molecular species and attachment of a bio-molecular species (Heparin) to said non bio-molecular species, substantially increases the time required for clotting to take place in the blood plasma. From the figures given above the increase in clotting time as compared with the untreated PET sample in plasma, is seen to be increased by approximately a factor of four.

What is claimed is:

1. A method of producing a functionalised polymer, comprising steps of reacting a polymer in aqueous medium with a water soluble azo compound to produce oxygen-centred radicals, wherein said radicals are responsible for introducing functional groups into the polymer.

2. A method according to claim 1, wherein the polymer is selected from the group consisting of olefin polymers, aliphatic polymers, polymers that contain an aromatic ring, carbonate polymers, vinyl polymers, polyurethanes, nylons, polyglycols or polyaldehydes.

3. A method according to claim 1, carried out in the absence of any additive which is preferentially oxidised or is reactive towards the radicals produced by the azo compounds.

4. A method according to claim 1, wherein no cationic surfactants are added.

5. A method according to claim 1, wherein an additional oxidising agent is added.

6. A method according to claims 5, wherein additional oxidising agent is oxygen gas.

7. A method according to claims 1, wherein said azo compound is 4,4'-azobis (cyanovaleric acid) or 2,2'-azobis (2-methylpropionamidine) dihydrochloride.

8. A method according to claim 1, wherein a bio-molecular species (such as heparin) is attached to the functionalised polymer.

9. A method according to claim 1, wherein the functionalised polymer is fabricated as a medical device or as a prosthetic device.

10. A method of producing a functionalised polymer selected from the group consisting of olefin polymers, aliphatic polymers, polymers that contain an aromatic ring, carbonate polymers, vinyl polymers, polyurethanes, nylons, polyglycols or polyaldehydes fabricated as a medical device or as a prosthetic device, comprising steps of reacting the polymer in an aqueous medium with a water soluble azo compound in the absence of any additive which is preferentially oxidised or is reactive towards the radicals produced by the azo compound to produce oxygen-centred radicals, and introducing bio-molecular species into the polymer by means of said functional groups.

* * * * *

UNITED STATES PATENT AND TRADEMARK OFFICE
CERTIFICATE OF CORRECTION

PATENT NO. : 6,369,168 B1
DATED : April 9, 2002
INVENTOR(S) : Al-Lamee et al.

It is certified that error appears in the above-identified patent and that said Letters Patent is hereby corrected as shown below:

Title page,
Item [57], ABSTRACT,
Line 2, "prostheses" should read -- prosthesis --

Column 1,
Line 22, "biomaterals" should read -- biomaterials --
Line 23, "problem Thus" should read -- problem. Thus --
Line 25, "and" should be deleted Column 2,
Line 2, "consisting olefin" should read -- consisting of olefin --
Line 46, "acylamide" should read -- acrylamide --

Column 5,
Line 3, "cental" should read -- central --
Line 7, "dimetylcarboxy" should read -- dimethylcarboxy --
Line 12, "4-cyanovalerc" should read -- 4-cyanovaleric --
Line 47, "lie" should read -- lies --

Column 10,
Line 13, "carbodimide" should read -- carbodiimide --
Line 45, "dot" should read -- clot --

Column 11,
Line 16, "claims 1" should read -- claim 1 --

UNITED STATES PATENT AND TRADEMARK OFFICE
CERTIFICATE OF CORRECTION

PATENT NO. : 6,369,168 B1
DATED : April 9, 2002
INVENTOR(S) : Al-Lamee et al.

It is certified that error appears in the above-identified patent and that said Letters Patent is hereby corrected as shown below:

<u>Column 12,</u>
Line 11, "steps" should read -- the steps --

Signed and Sealed this

Nineteenth Day of November, 2002

*Attest:*

*Attesting Officer*

JAMES E. ROGAN
*Director of the United States Patent and Trademark Office*